United States Patent [19]

Decher et al.

[11] Patent Number: 4,973,429
[45] Date of Patent: Nov. 27, 1990

[54] ORGANIC MATERIALS WITH NON-LINEAR OPTICAL PROPERTIES

[75] Inventors: Gero Decher, Walluf, Fed. Rep. of Germany; Bernd Tieke, Marly; Christian Bosshard, Baden, both of Switzerland; Peter Günter, Riedt-Neerach, Switzerland

[73] Assignee: Ciba-Geigy Corporation, Ardsley, N.Y.

[21] Appl. No.: 311,482

[22] Filed: Feb. 15, 1989

[30] Foreign Application Priority Data

Feb. 17, 1988 [CH] Switzerland .......................... 576/88

[51] Int. Cl.$^5$ ...................... F21V 9/04; C07D 211/78; C07D 211/90; C07C 201/00
[52] U.S. Cl. .................................. 252/587; 252/589; 252/582; 546/286; 546/288; 546/289; 546/298; 546/304; 546/307; 546/310; 546/313; 546/315; 546/346; 568/924
[58] Field of Search ............... 252/582, 587, 589, 600; 546/286, 288, 289, 298, 304, 307, 310, 313, 315, 346; 568/924

[56] References Cited

U.S. PATENT DOCUMENTS

| | | | |
|---|---|---|---|
| 3,132,019 | 5/1964 | Soper | 546/307 |
| 3,634,439 | 1/1972 | Ayad et al. | 546/307 |
| 3,826,608 | 7/1974 | Wiskott et al. | 546/307 |
| 3,943,125 | 3/1976 | Gerber | 260/240 D |
| 4,091,025 | 5/1978 | Schlesinger et al. | 546/307 |
| 4,728,576 | 3/1988 | Gillberg-LaForce et al. | 428/411.1 |
| 4,792,208 | 12/1988 | Ulman et al. | 350/96.34 |
| 4,796,971 | 1/1989 | Robello et al. | 350/96.34 |
| 4,796,981 | 1/1989 | Nishimura et al. | 252/582 X |

FOREIGN PATENT DOCUMENTS

| | | |
|---|---|---|
| 0203780 | 12/1986 | European Pat. Off. . |
| 0255718 | 2/1988 | European Pat. Off. . |
| 0299921 | 1/1989 | European Pat. Off. . |
| 329613 | 8/1989 | European Pat. Off. ............ 252/587 |
| 2339993 | 8/1972 | Fed. Rep. of Germany ...... 546/304 |
| 2655144 | 6/1978 | Fed. Rep. of Germany ...... 546/307 |
| 1566125 | 3/1969 | France .................... 546/307 |
| 62-187828 | 8/1987 | Japan . |
| 1-040463 | 2/1989 | Japan . |
| 687073 | 7/1977 | U.S.S.R. ............... 546/304 |
| 1331228 | 9/1973 | United Kingdom . |
| 01473 | 2/1989 | World Int. Prop. O. .......... 546/307 |

OTHER PUBLICATIONS

Bosshard, C. et al., Proc. SPIE-Int. 1017, 141, 1989.
Decher, G. et al., J. Chem. Soc. Chem. Comm., 14, 933, 1988.
Popovitz-Biro, R. et al., J. Am. Chem. Soc., 110(8), 2672, 1988.
Schilling, M. et al., J. Org. Chem. 53(23), 5538, 1988.
Fuhrhop, J. et al., Liebigs Ann. Chem. (5) 802, 1983.
Moss, R. et al., J. Org. Chem. 39, 1083, 1974.
Nonlinear Optical Properties of Organic Molecules and Crystals, vol. 1, D. S. Chemla et al., Assoc. Press., Orlando, Fla., pp. 227–296, (1987).
Derwent Abstract-JP-A-60, 178 427.
Sou. Tech. Phys. Lett., 11, 249–250.
Optics Comm., 61, 351–316, 1987.
J. Opt. Soc. Am. B, 4, 950–954, 1987.
Electr. Lett. 22, 460–462, 1986.
Thin Solid Films, 132, 101–112, 1985.
Angew. Chem., 96, 637–651, 1984.
J. Opt. Soc. Am. B, 4, 998–1012, 1987.
Appl. Optics, 26, 211–233, 1987.
J. Opt. Soc. Am. B, 5, 300–308, 1988.
J. C. S. Chem. Comm., 14, 933, 1988.

Primary Examiner—John S. Maples
Assistant Examiner—Richard Treanor
Attorney, Agent, or Firm—Stephen V. O'Brien

[57] ABSTRACT

A material in the form of a film is described which contains, in an orientated arrangement which does not display point symmetry, compounds of formula I

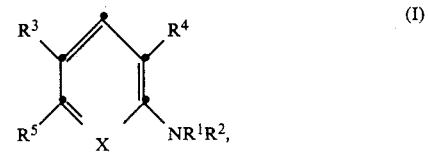

wherein X is =CH— or =N—, $R^1$ is $C_{12}$–$C_{30}$-alkyl, $R^2$ is hydrogen or $C_1$–$C_{30}$-alkyl, $R^3$ is —$NO_2$, —CN, —$CF_3$, —$COCF_3$, —$SO_2CH_3$ or —$SO_2CF_3$, $R^4$ is hydrogen or is defined in the same way as $R^3$, $R^5$ is hydrogen or —$NR^6R^7$ and $R^6$ and $R^7$ independently of one another are hydrogen or $C_1$–$C_{30}$-alkyl, it also being possible for any of the alkyl radicals to be partially fluorinated or perfluorinated.

The compounds of formula I can be arranged in Langmuir-Blodgett layer systems. Such systems can be used for example for the manufacture of opto-electronic units.

4 Claims, No Drawings

ORGANIC MATERIALS WITH NON-LINEAR OPTICAL PROPERTIES

The present invention relates to organic materials in a selected arrangement, in particular in the form of Langmuir-Blodgett layer systems, to selected compounds, to a frequency doubling process and to the use of these materials in opto-electronic units.

It is known that, in non-linear optical materials (NLO materials), electromagnetic fields are transformed by interaction with the material into new electromagnetic fields of different phase, amplitude, frequency and propagation characteristic.

In recent years, such materials have aroused considerable interest as potential components of electro-optical units. In these materials, the polarization p caused by an electric field is a function of the linear and non-linear terms of the electric field strength E $$P = \chi^{(1)} \cdot E + \chi^{(2)} \cdot E^2 + \chi^{(3)} \cdot E^3 + \ldots$$

In this equation, $\chi^{(i)}$ ($i=1, 2, 3 \ldots$) is the electric susceptibility, which in turn is a function of molecular parameters and the arrangement of the molecules. To produce second-order non-linear optical effects, $\chi^{(2)}$ must by definition be non-zero. Examples of such effects are frequency doubling, optical rectification and the so-called Pockels effect.

It is known that, to produce second-order non-linear optical effects, suitable materials have to be orientated but must not display point symmetry; the individual molecules must therefore possess no point symmetry elements and also they must not arrange themselves (for example in a crystal) in such a way as to give rise to point symmetry or isotropy.

Another requirement of NLO materials is the absence of strong absorption bands in the region of the generating or transformed radiation, since absorption in the region of the generating radiation may destroy the material and absorption in the region of the transformed radiation would reduce the effects which can be achieved Thus there is a particular need for organic NLO materials which absorb at the shortest possible wavelength (so-called cut-off wavelength).

One possible way of producing a specific arrangement of organic molecules is the Langmuir-Blodgett process (LB process), in which monomolecular films of amphiphilic compounds are transferred successively onto solid substrates.

Other possible ways of producing a specific arrangement of organic molecules is orientation in polymer films [q.v. J. D. Williams in "Angewandte Chemie", 96, 637–651 (1984)] or the preparation of inclusion compounds, as described in Japanese patent application No. A-60-178,427.

Langmuir-Blodgett layer systems (LB systems) with non-linear optical properties are already known. These systems contain amphiphilic merocyanins, hemicyanins or azobenzenes as active materials. Examples of such systems can be found in J. Opt. Soc. Am., B4(6), 950–4 (1987), Electronics Letters, 22(9), 460–2 (1986), Thin Solid Films, 132, 101–12 (1985), Sov. Techn. Phys. Lett., 11(5), 250 (1985), Opt. Communic., 61(5), 351–6 (1987), and in European patent application No. A-203,780.

Amphiphilic compounds have now been found which can easily be arranged in films without displaying point symmetry, which possess a short cutoff wavelength and which have a high efficiency in frequency doubling.

The present invention relates to a material in the form of a film containing, in an orientated arrangement which does not display point symmetry, compounds of formula I

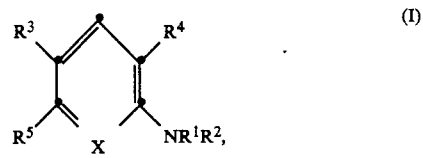

wherein X is =CH— or =N—, $R^1$ is $C_{12}$–$C_{30}$-alkyl, $R^2$ is hydrogen or $C_1$–$C_{30}$-alkyl, $R^3$ is —$NO_2$, —CN, —$CF_3$, —$COCF_3$, —$SO_2CH_3$ or —$SO_2CF_3$, $R^4$ is hydrogen or is defined in the same way as $R^3$, $R^5$ is hydrogen or —$NR^6R^7$ and $R^6$ and $R^7$ independently of one another are hydrogen or $C_1$–$C_{30}$-alkyl, it also being possible for any of the alkyl radicals to be partially fluorinated or perfluorinated.

The expression "material in the form of a film containing . . . in an orientated arrangement which does not display point symmetry" is understood as meaning quite generally any material in the form of a film in which at least part of the compounds of formula I is orientated and is fixed in an arrangement which does not display point symmetry. Such an arrangement of these compounds results in polar films (macroscopic dipole moment)

These materials may be solid or liquid-crystalline film-forming materials; the material may also be a mixture containing compounds of formula I in dissolved form or in the form of molecular aggregates in a carrier material, or the material may consist essentially of the compounds of formula I.

Examples of anisotropic mixtures of compounds of formula I are mixtures in low-molecular or polymeric materials which are generally below their melting point or their glass transition temperature. Examples are mixtures of orientated compounds of formula I in polymer films (obtainable e.g. by orientation of the compounds by means of an electric field above the glass transition temperature of the carrier polymer, followed by freezing-in of the orientated compounds by cooling below the glass transition temperature; q.v. the above-mentioned article by D. J. Williams).

However, the said materials can also be microcrystalline films of the compounds of formula I. In these cases, an NLO activity will only be observable when the unit cell of the microcrystals displays no point symmetry elements.

The relationship between molecular structure and crystal structure is generally not predictable, so it must be up to the person skilled in the art, in each individual case, to check the NLO properties of a microcrystalline film of compounds of formula I from the known NLO effects.

Using the LB technique, an arrangement of the compounds of formula I which does not display point symmetry can generally always be obtained For this reason, the invention preferably relates to a material in which the compounds of formula I are arranged in the form of Langmuir-Blodgett layer systems (LB systems).

To prepare these LB systems, a small amount of a solution of a compound of formula I in a low-boiling solvent is applied to a free water surface in a manner known per se, the solvent is allowed to evaporate and the resulting film is compressed to form a stable monomolecular layer on the water surface.

It is known that the stability of the films can be influenced by the choice of experimental parameters. Thus it is possible, for example, to stabilize films of relatively short-chain compounds of formula I by cooling the subphase, or compounds of formula I are used in combination with other amphiphilic compounds capable of forming stable monomolecular films on the water surface or of stabilizing monomolecular films.

Examples of such compounds are long-chain carboxylic acids such as palmitic acid, stearic acid, arachidic acid or behenic acid, or the esters, in particular the methyl esters, or the amides of these acids; long-chain primary amines such as n-hexadecylamine, n-octadecylamine or n-eicosylamine; long-chain alcohols such as n-hexadecanol, n-octadecanol or n-eicosanol; long-chain hydrocarbons such as hexadecane, octadecane or eicosane; or steroids and steroid derivatives such as cholesterol.

It is also possible to use amphilic compounds containing polymerizable groups, examples being ω-tricosenoic acid, diacetylene-carboxylic acids or long-chain sorbic acid esters. A further possibility is to use film-forming polymers which are spread over the water surface and then transferred, an example being polystearoylhydroxyethyl methacrylate.

The compounds of formula I are generally present in such mixtures in a proportion of at least 1% by weight, based on the total mixture.

Monomolecular layers on the water surface can be transferred onto solid supports by the Langmuir-Blodgett process (LB process). To do this, a solid support with an essentially smooth surface is dipped in a manner known per se through a compressed monomolecular film on a water surface, the said film thereby being transferred onto the support.

Multilayer systems can be prepared in this way by dipping and retracting the support several times.

The layer on the water surface can be changed after every dipping process, making it possible to prepare different sequences of layers on the support.

Depending on the hydrophilicity or hydrophobicity of the support surface, the support is coated in the first dipping process (hydrophobic support) or retraction process (hydrophilic support). For hydrophilic supports, the polar groups come into contact with the support surface, whereas in the case of hydrophobic supports, the hydrophobic radicals $R^1$ and $R^2$ come into contact with the support surface. These procedures are known per se to the person skilled in the art of LB systems.

A very wide variety of substrates with a microscopically planar surface are suitable as solid supports for the LB process. Examples are metals such as aluminium, copper, silver or gold, semiconductors such as germanium, silicon or GaAs, inorganic materials such as glass, quartz, $KNbO_3$, $LiNbO_3$, ZnSe or $Si_2N_3$, or plastics such as Teflon ®, polyethylene, polypropylene, polymethyl methacrylate or polyesters. It is also possible to use supports which have been rendered hydrophobic, for example glass or quartz which has been pretreated with trichloromethylsilane, dichlorodimethylsilane or trichlorooctadecylsilane.

The subphase on which the monomolecular layer is formed generally consists of multidistilled water to which small amounts of salts, for example $CdCl_2$ or $BaCl_2$, are added, if desired, in order to stabilize the films. The subphase can also contain buffer substances, for example $NaHCO_3$. These modifications are known to the person skilled in the art and are selected according to the type of film-forming substances.

Multilayers can be prepared by the LB process from pure dye monolayers or from mixed films containing compounds of formula I and other film-forming materials. These layers can follow one another in direct succession or dye monolayers can alternate with layers of other layer-forming materials which are not necessarily NLO-active.

Multilayer systems of the X, Y or Z type can be built up by transferring monolayers. These multilayer systems are known per se to the person skilled in the art and are described for example in "Techniques of Chemistry, Physical Methods of Chemistry, Vol. I, Part IIIB, p. 666–669".

They can be prepared either by always transferring films of one and the same NLO-active material (films containing compounds of formula I) or by transferring different films and thereby producing alternating layer sequences.

The following three variants are preferred in the case of alternating layer sequences:
(a) An NLO-active film or an NLO-active mixed film is transferred in the dipping process and an NLO-inactive film or an NLO-inactive mixed film is transferred in the retraction process.
(b) An NLO-inactive film or mixed film is transferred in the dipping process and an NLO-active film or mixed film is transferred in the retraction process.
(c) NLO-active films or mixed films are transferred in both dipping and retraction processes, these films alternately containing compounds of formula I with dipole moments of different orientation.

The thickness of the LB layer systems of the invention generally ranges from 3 nm to 5 μm.

Preferred LB systems of alternating or non-alternating layers are those which contain, as the NLO-active material, a compound of formula I wherein X is =CH—, $R^1$ is $C_{18}$–$C_{22}$-alkyl, $R^2$ is hydrogen or $C_{18}$–$C_{22}$-alkyl, $R^3$ is —$NO_2$, $R^4$ is hydrogen or —$NO_2$ and $R^5$ is hydrogen or —$NH_2$.

Preferred LB systems are those which contain, as the NLO-active material, a compound of formula I wherein X is =N—.

Systems of these compounds are distinguished by an especially high NLO activity.

Especially preferred LB systems are those which contain alternating or, preferably, non-alternating layers of compounds of formula I wherein X is =N—, $R^1$ is $C_{16}$–$C_{26}$-alkyl, $R^2$ is hydrogen, $R^3$ is —$NO_2$, $R^4$ is hydrogen or —$NO_2$ and $R^5$ is hydrogen; the derivative of formula I wherein $R^1$ is $C_{22}$-alkyl is most preferred in this embodiment.

The compounds of formula I wherein X is =N— are novel and also represent a subject of the present invention.

Any alkyl radicals can be linear or branched radicals, linear radicals being preferred.

The alkyl radicals can also be partially fluorinated or perfluorinated or they can have one or more trans double bonds or triple bonds which are not in the 1-position. Several trans double bonds or triple bonds can be isolated or conjugated with one another. Specific examples of alkyl radicals are methyl, ethyl, n-propyl, isopropyl, n-butyl, isobutyl, n-pentyl, n-hexyl, n-heptyl, n-octyl, 2-ethylhexyl, n-nonyl, n-decyl, n-undecyl, n-dodecyl, n-tridecyl, n-tetradedcyl, n-pentadecyl, n-hexadecyl, n-heptadecyl, n-heptadecyl, n-octadecyl, n-nonadecyl, n-eicosyl, n-heneicosyl, n-docosyl, n-tetracosyl, n-hexacosyl, n-octacosyl and n-triacontyl, as well as the corresponding perfluorinated derivatives or allyl, propargyl, octadec-9-trans-enyl, ω-tricosenyl or pentacosa-10,12-diynyl.

$R^1$ and $R^2$ are preferably radicals of the formula $-C_pH_{2p+1}$, wherein p is 12-30, preferably 16-26 and most preferably 20-24. Such radicals are preferably linear.

$R^1$ and $R^2$ must have a certain minimum length so that stable monomolecular films can be formed from compounds of formula I on the water surface. If $R^2$ is hydrogen or a short-chain alkyl radical having fewer than 12 C atoms, $R^1$ should have at least 18 C atoms.

$R^3$ is preferably $-NO_2$ or $-COCF_3$ and most preferably $-NO_2$. $R^4$ is preferably hydrogen or $-NO_2$.

The compounds of formula I can be prepared from the appropriate fluorobenzene or chlorobenzene derivatives or the appropriate fluoropyridine or chloropyridine derivatives by reaction with the appropriate amines in order to effect the nucleophilic exchange of halogen atoms for amino groups.

Examples of such reactions on fluorobenzene derivatives containing electron-attracting substituents can be found in "Chromatographia, 14(5), 289–95 (1981)".

Exchange reactions on 2-halogenodinitropyridines are described in "Bull. Acad. Polon. Ser Sci. Chim., XVI(1), 7–12 (1968)".

The choice of reaction conditions for the nucleophilic exchange reactions is known per se. In general, a solution of the aromatic halogen compound in an inert organic solvent is placed in the reaction vessel and the amine is added dropwise, or the reaction is carried out under pressure, for example when reacting the aromatic halogen compound with ammonia.

A selection of possible reaction parameters can be found in "Methoden der organischen Chemie (Methods of organic chemistry) (Houben-Weyl), Vol. XI/1, p. 24–36, G. Thieme Verlag, Stuttgart (1957)".

A survey of the choice of reaction conditions in the case of pyridine derivatives can be found in "The Chemistry of Heterocyclic Compounds: Pyridine and its Derivatives, Part III, Vol. IX, p. 5–7".

The amines used in the nucleophilic exchange reactions are known per se or can be prepared by known processes.

Primary amines are obtained for example by alkylating phthalimides and then hydrolyzing the products to give the amines. Secondary amines are obtained for example by reducing N-monoalkylated amides with $LiAlH_4$.

Some of the halogenonitrobenzene or halogenonitropyridine starting materials for the nucleophilic exchange reactions are known and are commercially available. Such compounds can be prepared by introducing one or two nitro groups into the appropriate halogenobenzenes or halogenopyridines in a manner known per se.

The halogenotrifluoromethylbenzene, halogenotrifluoromethylpyridine, halogenocyanobenzene and halogenocyanopyridine starting materials can be prepared from the appropriate halogenocarboxylic acid derivatives by converting the —COOH group(s) into —$CF_3$ or —CN radicals. Such conversions are known per se.

Conversion of the —COOH group(s) into —$CF_3$ radicals can be carried out for example by reaction with $SF_4$. Such reactions can be found for example in "Methoden der organischen Chemie (Methods of organic chemistry) (Houben-Weyl), Vol. V/3, p. 88–93, G. Thieme Verlag, Stuttgart (1962)".

Conversion of a —COOH group into a —CN radical can be effected in a manner known per se by converting the carboxyl group into the carboxamide group and then reducing the latter to the nitrile. Some of the halogenotrifluoromethylcarbonylbenzene or halogenotrifluoromethylcarbonylpyridine starting materials are known or can be obtained by processes known per se.

Thus the $CF_3$—CO group can be introduced for example by Friedel-Crafts acylation of the appropriate halogenobenzene or halogenopyridine derivatives with $(CF_3-CO)_2O$.

The halogenotrifluoromethylsulfonylbenzene or halogenotrifluoromethylsulfonylpyridine starting materials can be obtained in a similar manner, for example by reacting the appropriate halogenobenzene or halogenopyridine derivatives with $(CF_3-SO_2)_2O$. Such reactions are described in J. Org. Chem., 42(24), 3875-7 (1977).

The halogenomethylsulfonylbenzene or halogenomethylsulfonylpyridine starting materials can be obtained from the appropriate halogenobenzenes or halogenopyridines by Friedel-Crafts acylation with $SO_2$, salting-out of the resulting sulfinic acid derivative with NaCl and subsequent methylation of the sodium sulfinate with methyl halides or dimethyl sulfate. Such reactions are described for example in "Methoden der organischen Chemie (Methods of organic chemistry) (Houben-Weyl), Vol. IX, p. 231-3 and 324–5, G. Thieme Verlag, Stuttgart (1955)".

In addition to the nucleophilic exchange reactions, the compounds of formula I can also be prepared by introducing the radicals $R^3$ and, if necessary, $R^4$ into the appropriate amino derivatives. 3,5-Dinitro-2,6-diaminopyridines, for example, can be obtained in this way. Such reactions are known for example from U.S. Pat. No. 3,943,125.

The above-described conversions of —COOH into —$CF_3$ or —CN or the introductions of —CO—$CF_3$, —$SO_2$—$CF_3$ or —$SO_2$—$CH_3$ into the appropriate aminocarboxybenzene or aminocarboxypyridine derivatives can also be used to prepare the compounds of formula I.

The compounds of formula I can be used for the manufacture of optoelectronic units, preferred fields of application are frequency doublers or waveguides.

The invention further relates to the use of the compounds of formula I for these purposes.

The following Examples illustrate the invention.

(A) PREPARATIVE EXAMPLES

Example 1: Synthesis of 2-hexadecylamino-5-nitropyridine 1

0.5 g (3.2 mmol) of 2-chloro-5-nitropyridine (Fluka, purum), 0.76 g (3.2 mmol) of hexadecylamine (Merck-Schuchard, for synthesis) and 1 g of $NaHCO_3$ are weighed out and suspended in 10 ml of $CHCl_3$/DMF 1:1 (puriss., for analysis). The suspension is heated to 100° C. (bath temperature) and stirred for 4 hours at this temperature. When the reaction mixture has cooled, water is added and extraction is carried out with diethyl ether. The organic phase is extracted twice with water and dried over $Na_2SO_4$. After evaporation of the solvent, the residue is chromatographed on 50 times the amount of silica gel (eluent=hexane/ether 95:5). The slightly yellowish product fraction is concentrated and 1 is recrystallized again from hexane/ether.

This yields 0.94 g of yellowish crystals (81%) melting between 76° and 78° C.

The elemental analysis data of 1 are listed in Table 1.

Examples 2–6: Synthesis of 2-octadecylamino-5-nitropyridine 2, 2-eicosylamino-5-nitropyridine 3, 2-docosylamino-5-nitropyridine 4, 2-tetracosylamino-5-nitropyridine 5 and 2-hexacosylamino-5-nitropyridine 6

The synthesis procedure is essentially as described under Example 1.

Octadecylamine (Fluka) is recrystallized several times from ethanol before the synthesis of 2.

Eicosylamine, docosylamine, tetracosylamine and hexacosylamine are known from the literature but are not commercially available. They are prepared by standard methods from the corresponding carboxylic acids (conversion of the carboxylic acid into the acid chloride with $SOCl_2$, reaction with $NH_3$ in tetrahydrofuran to give the acid amide, and reduction with $LiAlH_4$ in tetrahydrofuran to give the amine). The crude amines are purified by recrystallization several times from ethanol.

As the solubility of 2-alkylamino-5-nitropyridines in hexane/ether decreases greatly with increasing alkyl chain length, the compounds 3 to 6 are not purified by chromatography. In these cases, the crude products are purified by recrystallization several times from ethanol. The yields of end product are between 60 and 80% in all cases.

The elemental analysis data and the melting points of 2-6 are listed in Table 1.

Example 7: Synthesis of 2-octadecylamino-3,5-dinitropyridine 7

The synthesis is carried out analogously to Example 1 using 2-chloro-3,5-dinitropyridine (Fluka) and octadecylamine as the starting materials. Octadecylamine is recrystallized several times from ethanol before the synthesis.

This yields, after chromatography, 0.64 g of yellowish crystals (46% of theory) melting at 74°-77° C. The elemental analysis data of 7 are listed in Table 2.

Example 8: Synthesis of 2-N,N-bis(octadecyl)amino-5-nitropyridine 8

The synthesis is carried out analogously to Example 1 using 2-chloro-5-nitropyridine (Fluka) and N,N-bis(octadecyl)amine (Fluka, 97%) as the starting materials.

This yields, after chromatography, 1.70 g of yellow crystals (88% of theory) melting at 65°-68° C. The elemental analysis data of 8 are listed in Table 2.

Example 9: Synthesis of 2-N,N-bis(octadecyl)amino-3,5-dinitropyridine 9

The synthesis is carried out analogously to Example 1 using 2-chloro-3,5-dinitropyridine (Fluka) and N,N-bis(octadecyl)amine (Fluka, 97%) as the starting materials.

This yields, after chromatography, 0.96 g of yellow crystals (43% of theory) melting at 36°-41° C. The elemental analysis data of 9 are listed in Table 2.

Example 10: 2-N-Methyldocosylamino-5-nitropyridine 10

The procedure is as described under Examples 2–6, 2-chloro-5-nitropyridine being reacted with N-methyldocosylamine. The yield is 69% of theory. The product melts at 88°-90° C. The elemental analysis data of 10 are listed in Table 2.

Example 11: Synthesis of 4-nitro-N-octadecylaniline 11

The synthesis is carried out analogously to Example 1 using 1-fluoro-4-nitrobenzene (Fluka, purum) and octadecylamine (Fluka) as the starting materials. Octadecylamine is recrystallized several times from ethanol before the synthesis.

This yields 0.78 g (62% of theory) of yellow crystals melting at 78°-80° C. The elemental analysis data of 11 are listed in Table 3.

Example 12: Synthesis of 2,4-dinitro-N-octadecylaniline 12

The synthesis is carried out analogously to Example 1 using 2,4-dinitrofluorobenzene (Fluka, puriss., for analysis) and octadecylamine (Fluka) as the starting materials.

This yields, after chromatography, 0.93 g of light yellow crystals (66% of theory) melting at 58°-59° C. The elemental analysis data of 12 are listed in Table 3.

Example 13: Synthesis of 2,4-dinitro-N,N-bis(octadecyl)aniline 13

The synthesis is carried out analogously to Example 1 using 2,4-dinitrofluorobenzene (Fluka, puriss., for analysis) and N,N-bis(octadecyl)amine (Fluka, 97%) as the starting materials.

This yields, after chromatography, 1.12 g of yellow crystals (50% of theory) melting at 40°-42° C. The elemental analysis data of 13 are listed in Table 3.

Examples 14–15: Synthesis of 2,4-dinitro-5-amino-N-octadecylaniline 14 and 2,4-dinitro-5-amino-N-docosylaniline 15

The synthesis is carried out analogously to Example 1 using 2,4-dinitro-5-fluoroaniline (Fluka, puriss., for analysis) and octadecylamine (Fluka) or docosylamine (see Examples 2–6) as the starting materials. The crude products are extracted with chloroform instead of ether.

This yields, after recrystallization from ethanol, 1.18 g of 14 (82% of theory) or 1.37 g of 15 (85% of theory) in the form of yellowish crystals. The characteristic data are listed in Table 3.

Example 16: Synthesis of 2,4-dinitro-5-amino-N,N-bis(octadecyl)aniline 16

The synthesis is carried out analogously to Example 1 using 2,4-dinitro-5-fluoroaniline (Fluka, puriss., for analysis) and N,N-bis(octadecyl)amine (Fluka, 97%) as the starting materials.

This yields 1.65 g (71% of theory) of a yellowish orange waxy substance melting at 53°-56° C. The elemental analysis data of 16 are listed in Table 3.

Example 17: 2,4-Dinitro-5-amino-N-methyl-N-docosylaniline 17

The procedure is as described under Examples 14–15, 2,4-dinitro-5-fluoroaniline being reacted with N-methyldocosylamine. The yield is 48% of theory. The product melts at 87°–89° C. The elemental analysis data of 17 are listed in Table 3.

Example 18: 4-Trifluoroacetyl-N-octadecylaniline 18

The synthesis is carried out analogously to Example 1 using 4-fluorotrifluoroacetophenone (prepared according to J. Org Chem. 32 (1967) 1311) and octadecylamine (Fluka) as the starting materials. Octadecylamine is recrystallized several times from ethanol before the synthesis. Pure DMF is used in the synthesis instead of the solvent mixture $CHCl_3/DMF$ (1:1).

The crude product (1.05 g) is recrystallized twice from ethanol and filtered on silica gel (ether/hexane). This yields 0.47 g of colourless to slightly yellowish crystals melting at 73°–75° C.

Analysis: Calculated for $C_{26}H_{42}NOF_3$ (441.63): C 70.71%, H 9.59%, N 3.17%, Found: C 70.93%, H 9.77%, N 3.14%.

Example 19: 4-Trifluoroacetyl-N-docosylaniline 19

The synthesis is carried out analogously to Example 18 using docosylamine as the amine. This yields 0.57 g of colourless to slightly yellowish crystals melting at 75°–77° C.

Analysis: Calculated for $C_{30}H_{50}NOF_3$ (497.73): C 72.39%, H 10.13%, N 2.81%, Found: C 72.34%, H 10.05%, N 2.78%.

Example 20: 4-Trifluoroacetyl-N-tetracosylaniline 20

The synthesis is carried out analogously to Example 18 using tetracosylamine as the amine. This yields 0.32 g of colourless to slightly yellowish crystals melting at 89°–90° C.

Calculated for $C_{32}H_{54}NOF_3$ (525.78): C 73.10%, H 35%, N 2.66%, Found: C 72.97%, H 10.30%, N 2.61%.

(B) PRODUCTION OF MONOLAYERS AND MULTILAYERS BY THE LB TECHNIQUE

Example 21: Production of monolayers at the gas/water interface

Monolayers are produced at the gas/water interface using a preparative Lauda film balance. The high-purity water required is freshly prepared with a Milli-Q unit from Millipore. The monomolecular film is produced by allowing drops of a fresh spreading solution (concentration of the amphiphile in $CHCl_3$ (Merck-Uvasol)=1±0.5 mg/ml) to fall onto the water surface according to standard techniques. Each time after the solvent has evaporated, force/area diagrams are recorded at different temperatures (compression rate=12.3 cm²/min). The characteristic data determined are the collapse pressure $F_c$ and the collapse area $A_c$ of the monolayer at the relevant temperature (see Table 4).

Example 22: Production of monolayers of mixtures of amphiphiles at the gas/water interface The procedure for producing monolayers of mixtures of amphiphiles is as described under Example 21. A common solution of two or more amphiphiles of defined composition is used as the spreading solution (total concentration of the amphiphiles in $CHCl_3$ (Merck-Uvasol)=1±0.5 mg/ml). The composition and characteristic data of these monolayers are listed in Table 5.

Example 23: Production of LB multilayers of pure amphiphiles

On a subphase of pure water at the temperature T, a monomolecular layer is produced analogously to Example 21 and compressed to the film pressure $F_t$. T and $F_t$ are optimized for each substance so that the monolayer is in a stable condensed phase. A solid support is then dipped vertically through the monolayer into the subphase, and retracted, at the dipping speed $s_1$. The support is then dipped and retracted several more times at the dipping speed $s_2$, where $s_2=2s_1$ to $3s_1$. A monolayer is transferred in each dipping process and the multilayer is thus built up by dipping several times. The substrates used and all the characteristic data are listed in Table 6. The $d_{001}$ values show that the multilayers have the Y structure in all Examples.

Example 24: Production of LB multilayers of the X type

On a subphase of pure water at a temperature of 20° C., a monomolecular layer of compound 14 is produced, analogously to Example 21, on a NIMA film balance for alternating layers and compressed to a film pressure of 30 mN/m. A glass support which has been rendered hydrophobic with octadecyltrichlorosilane is then dipped vertically through the monolayer into the subphase at a speed of 10 mm/min.

The support is retracted through a pure water surface so that a monolayer can only be transferred on dipping. The process is carried out 20 times. A multilayer of the X type with a thickness of 20 monolayers is formed. The multilayer is transparent and has an optical density of 0.0058 per monolayer (at $\lambda_{max}=422$ nm).

Example 25: Production of LB multilayers of mixtures of amphiphiles

On a subphase of pure water at the temperature T, a monomolecular layer is spread analogously to Example 22 and compressed to the film pressure $F_t$. T and $F_t$ are optimized for each substance so that the monolayer is in a stable condensed phase. The procedure for film transfer is as described in Example 23. The substrates used and all the characteristic data are listed in Table 7.

Example 26: Production of alternating LB multilayers

On a subphase of pure water at the temperature T, a monomolecular layer of compound 14 is produced analogously to Example 21 and compressed to a film pressure of 35 mN/m. A glass support which has been rendered hydrophobic with octadecyltrichlorosilane is then dipped vertically through the monolayer into the subphase at a dipping speed of 10 mm/min. The monomolecular layer is then sucked off the surface and a new monolayer of arachidic acid is spread and compressed to a film pressure of 35 mN/m. The glass support is now retracted at a speed of 2.5 mm/min. After the arachidic acid monolayer has been removed and the bottom edge of the support has completely dried (drying time≦60 min), the process described is repeated a further five times. An alternating multilayer with a total thickness of 12 monolayers is formed. The multilayer is transparent and has an optical density of 0.0078 per alternating double layer (at $\lambda_{max}=417$ nm).

Example 27: Measurement of the frequency doubling in LB multilayers

Silane-treated glass supports are coated analogously to Example 23 with different numbers of layers of substances 2–6 (cf. Tables 8 and 9). The LB films are then irradiated with an Nd-YAG laser (Quatronix 416, 2.3 kW at 1064 nm, pulse rate=500 Hz, pulse duration=350 ns, Q-switched) in the direction of the normals to the layers. The laser is focused onto the LB film with a collimating lens (focal length=80 mm). The beam diameter is about 21 μm (estimated intensity: 220 μW/cm²). The signal of the second harmonic (λ=532 nm) is detected by the method described by J. C. Baumert, J. Hoffnagle and P. Günter; Europ. Conf. on Opt. Syst. and Appl; Amsterdam 1984, SPIE Vol. 492, p. 374 et seq. The results are given in Tables 8 and 9.

A signal is measured for all LB films. $I^{2\omega}$ increases with the square of the number of layers (see Table 9). For the sample with 270 double layers of 4, the conversion rate $I^{2\omega}/I^{\omega}$ is $2.10^{-5}\%$ for the light vector parallel to the direction of dipping and $I^{2\omega}=220$ μW/cm².

Example 28: Measurement of waveguide properties in LB multilayers

Glass supports into which gratings with a spacing λ of 0.38 μm have been etched are treated with silane and coated with 50, 100 and 180 double layers of substance 4. The direction of dipping corresponds to the direction of the grating lines. The sample is irradiated with an He-Ne laser (λ=632.8 nm, 5 mW). The film is then rotated about the direction of dipping, perpendicular to the laser beam, until light is coupled into the LB film and transmission occurs. This is done with the light vector parallel and perpendicular to the direction of dipping. For the light vector parallel to the direction of dipping, the coupling angles and the effective refractive indices $N_{eff}$ for the different numbers of layers are given in Table 10.

TABLE 1

Characteristic data of the 2-alkylamino-5-nitropyridines 1-6 prepared

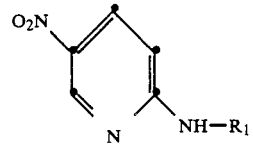

| Substance | R₁ | Melting point | C,H,N calc. | C,H,N found |
|---|---|---|---|---|
| 1 | —C₁₆H₃₃ | 76–78° | % C 69.38 | % C 69.33 |
|   |   |   | % H 10.26 | % H 10.18 |
|   |   |   | % N 11.56 | % N 11.47 |
| 2 | —C₁₈H₃₇ | 66–69° | % C 70.55 | % C 70.26 |
|   |   |   | % H 10.55 | % H 10.43 |
|   |   |   | % N 10.73 | % N 10.61 |
| 3 | —C₂₀H₄₁ | 80–82° | % C 71.55 | % C 71.43 |
|   |   |   | % H 10.81 | % H 10.96 |
|   |   |   | % N 10.01 | % N 9.92 |
| 4 | —C₂₂H₄₅ | 82–85° | % C 72.43 | % C 72.62 |
|   |   |   | % H 11.03 | % H 11.07 |
|   |   |   | % N 9.39 | % N 8.96 |
| 5 | —C₂₄H₄₉ | 85–88° | % C 73.21 | % C 73.32 |
|   |   |   | % H 11.23 | % H 11.39 |
|   |   |   | % N 8.83 | % N 8.57 |
| 6 | —C₂₆H₅₃ | 88–90° | % C 73.90 | % C 74.29 |
|   |   |   | % H 11.40 | % H 11.59 |
|   |   |   | % N 8.34 | % N 7.97 |

TABLE 2

Characteristic data of the alkylaminonitropyridines 7-10 prepared

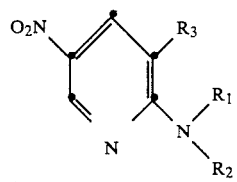

| Substance | R₁ | R₂ | R₃ | Melting point [°C.] | C,H,N calc. | C,H,N found |
|---|---|---|---|---|---|---|
| 7 | —C₁₈H₃₇ | —H | NO₂ | 74–77 | % C 63.27 | % C 63.45 |
|   |   |   |   |   | % H 9.24 | % H 9.15 |
|   |   |   |   |   | % N 12.83 | % N 12.84 |
| 8 | —C₁₈H₃₇ | —C₁₈H₃₇ | —H | 65–68 | % C 76.46 | % C 76.38 |
|   |   |   |   |   | % H 12.05 | % H 11.97 |
|   |   |   |   |   | % N 6.52 | % N 6.55 |
| 9 | —C₁₈H₃₇ | —C₁₈H₃₇ | —NO₂ | 36–41 | % C 71.46 | % C 71.25 |
|   |   |   |   |   | % H 11.12 | % H 11.01 |
|   |   |   |   |   | % N 8.13 | % N 8.26 |
| 10 | —C₂₂H₄₅ | —CH₃ | —H | 88–90 | % C 72.84 | % C 72.57 |
|   |   |   |   |   | % H 11.13 | % H 11.09 |
|   |   |   |   |   | % N 9.10 | % N 9.03 |

TABLE 3

Characteristic data of the nitro-N-alkylanilines 11–17 prepared

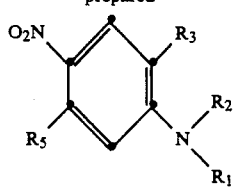

| Substance | $R_1$ | $R_2$ | $R_3$ | $R_5$ | M.p. [°C.] | C,H,N calc. | C,H,N found |
|---|---|---|---|---|---|---|---|
| 11 | —$C_{18}H_{37}$ | —H | —H | —H | 78–80 | % C 73.80 | % C 73.75 |
|  |  |  |  |  |  | % H 10.84 | % H 10.92 |
|  |  |  |  |  |  | % N 7.17 | % N 7.10 |
| 12 | —$C_{18}H_{37}$ | —H | —$NO_2$ | —H | 58–59 | % C 66.17 | % C 66.15 |
|  |  |  |  |  |  | % H 9.49 | % H 9.53 |
|  |  |  |  |  |  | % N 9.625 | % N 9.59 |
| 13 | —$C_{18}H_{37}$ | —$C_{18}H_{37}$ | —$NO_2$ | —H | 40–42 | % C 73.31 | % C 73.13 |
|  |  |  |  |  |  | % H 11.28 | % H 11.16 |
|  |  |  |  |  |  | % N 6.11 | % N 6.09 |
| 14 | —$C_{18}H_{37}$ | —H | —$NO_2$ | —$NH_2$ | 97–99 | % C 63.97 | % C 63.81 |
|  |  |  |  |  |  | % H 9.39 | % H 9.30 |
|  |  |  |  |  |  | % N 12.43 | % N 12.29 |
| 15 | —$C_{22}H_{45}$ | —H | —$NO_2$ | —$NH_2$ | 108–110 | % C 66.37 | % C 66.36 |
|  |  |  |  |  |  | % H 9.95 | % H 10.00 |
|  |  |  |  |  |  | % N 11.06 | % N 11.02 |
| 16 | —$C_{18}H_{37}$ | —$C_{18}H_{37}$ | —$NO_2$ | —$NH_2$ | 63–66 | % C 71.75 | % C 71.60 |
|  |  |  |  |  |  | % H 11.18 | % H 11.11 |
|  |  |  |  |  |  | % N 7.97 | % N 7.95 |
| 17 | —$C_{22}H_{45}$ | —$CH_3$ | —$NO_2$ | —$NH_2$ | 87–89 | % C 66.89 | % C 66.32 |
|  |  |  |  |  |  | % H 10.07 | % H 9.95 |
|  |  |  |  |  |  | % N 10.76 | % N 10.84 |

TABLE 4

Characteristic data of the monolayers of pure amphiphiles at the gas/water interface

| Example no. | Substance no. | Temp. of the subphase [°C.] | $F_c$ [mN/m] | $A_c$ [nm²/mol] |
|---|---|---|---|---|
| 21a | 1 | 5 | 11 | 0.32 |
| 21b | 2 | 9 | 20 | 0.32 |
| 21c | 3 | 15 | 29 | 0.32 |
| 21d | 4 | 15 | 39 | 0.31 |
| 21e | 5 | 20 | 46 | 0.29 |
| 21f | 6 | 20 | 54 | 0.29 |
| 21g | 8 | 5 | 18 | 0.40 |
| 21h | 11 | 10 | 8 | 0.40 |
| 21i | 13 | 4 | 8 | 0.50 |
| 21j | 14 | 18 | 49 | 0.22 |
| 21k | 15 | 28 | 50 | 0.22 |
| 21l | 16 | 10 | 47 | 0.41 |

TABLE 5

Characteristic data of the monolayers of mixtures of amphiphiles at the gas/water interface

| Example no. | Substances | Molar ratio in % | Temp. of the subphase [°C.] | $F_c$ [mN/m] | $A_c$ [nm²/mol] |
|---|---|---|---|---|---|
| 22a | methyl arachidate (MA) (Fluka, puriss.) and 4 | 33 67 | 20 | 24 | 0.26 |
| 22b | MA and 4 | 33 67 | 15 | 31 | 0.24 |

TABLE 6

Characteristic data of the LB films of pure amphiphiles

| Example no. | Substance no. | $F_t$ [mN/m] | Temp. of the subphase, T [°C.] | Substrate | Dipping speed $s_1$ [mm/min] | $s_2$ [mm/min] | Number of double layers transferred | $d_{001}$* [nm] | $\lambda_{max}$ of the monolayer [nm] |
|---|---|---|---|---|---|---|---|---|---|
| 23a | 2 | 9 | 9 | $C_{18}$-glass | 5 | 10 | 15 | 3.77 |  |
| 23b | 3 | 12 | 15 | $C_{18}$-glass | 15 | 30 | 18 | 4.11 | 374 |
| 23c | 4 | 19 | 15 | $C_{18}$-glass | 10 | 20 | 18 | 4.42 | 374 |
| 23d | 5 | 30 | 15 | $C_{18}$-glass | 20 | 40 | 18 | 4.73 | 374 |
| 23e | 6 | 27 | 20 | $C_{18}$-glass | 20 | 60 | 18 | 4.98 | 374 |
| 23f | 4 | 18 | 15 | $C_{18}$-quartz | 10 | 20 | 270 |  |  |
| 23g | 5 | 24 | 20 | $C_{18}$-quartz | 10 | 30 | 550 | 4.73 |  |
| 23h | 4 | 18 | 15 | $C_{18}$-Si single crystal | 10 | 20 | 18 | 4.36 |  |
| 23i | 4 | 20 | 15 | ZnSe | 10 | 30 | 100 |  |  |
| 23j | 8 | 10 | 5 | $C_{18}$-glass | 7.5 | 12.5 | 10 | 4.86 | 424 |
| 23k | 14 | 20 | 10 | $C_{18}$-glass | 7.5 | 15 | 20 | 5.33 |  |
| 23l | 16 | 18 | 15 | $C_{18}$-glass | 12.5 | 25 | 20 | 3.91 |  |

TABLE 6-continued

| | | | | | | | | |
|---|---|---|---|---|---|---|---|---|
| | | | Characteristic data of the LB films of pure amphiphiles | | | | | |
| | | | | Multilayers | | | | |
| | | | Temp. of the | | Dipping speed | Number of | | $\lambda_{max}$ of the |
| Example no. | Substance no. | $F_t$ [mN/m] | subphase, T [°C.] | Substrate | $s_1$ [mm/min] | $s_2$ [mm/min] | double layers transferred | $d_{001}$* [nm] | monolayer [nm] |
| 23m | 15 | 25 | 28 | $C_{18}$-glass | 15 | 20 | 15 | | |
| 23n | 4 | 18 | 15 | $C_{18}$-quartz | 15 | 30 | 5 | | 374 |
| 23o | 4 | 18 | 15 | $C_{18}$-quartz | 15 | 30 | 10 | | 374 |
| 23p | 4 | 18 | 15 | $C_{18}$-quartz | 15 | 30 | 15 | | 374 |
| 23q | 4 | 18 | 15 | $C_{18}$-quartz | 15 | 30 | 30 | | 374 |
| 23r | 4 | 18 | 15 | $C_{18}$-quartz | 15 | 30 | 45 | | 374 |
| 23s | 4 | 18 | 15 | $C_{18}$-quartz | 15 | 30 | 60 | | 374 |
| 23t | 4 | 18 | 15 | $C_{18}$-quartz | 15 | 30 | 90 | | 374 |
| 23u | 4 | 18 | 15 | $C_{18}$-quartz | 15 | 30 | 135 | | 374 |
| 23v | 4 | 18 | 15 | $C_{18}$-quartz | 15 | 30 | 400 | 4.37 | 374 |

*The thickness of a double layer, $d_{001}$, is determined by means of X-rays using a Philips powder diffractometer (Cu—$K_\alpha$ radiation).

TABLE 7

| | | | | | | | | | |
|---|---|---|---|---|---|---|---|---|---|
| | | | Characteristic data of the LB films of mixtures of amphiphiles | | | | | | |
| | | | | Multilayers | | | | | |
| Example no. | Substances of Example no. (see Table 5) | $F_t$ [mN/m] | Subphase T [°C.] | Substrate | $s_1$ [mm/min] | $s_2$ [mm/min] | Number of layers transferred | $d_{001}$* [nm] | Optical density per layer (at $\lambda_{max}$) |
| 25a | 22b | 18 | 15 | $C_{18}$-glass | 20 | 60 | 18 | 5.16 | 0.0048 (370 nm) |

*The thickness of a double layer, $d_{001}$, is determined by means of X-rays (cf. Table 6).

TABLE 8

Frequency doubling in LB layer systems of pure amphiphiles 2-6 (cf. Example 27)

| | Number of layers | $I^{2\omega}$(relative to 4=100) | |
|---|---|---|---|
| Substance | transferred | ∥* | ⊥* |
| 2 | 36 | 5 | 0.5 |
| 3 | 36 | 52 | 5 |
| 4 | 36 | 100 | 5 |
| 5 | 36 | 12 | 0.5 |
| 6 | 36 | 6 | 0.2 |

*Light vector parallel or perpendicular to the direction of dipping

TABLE 9

Frequency doubling in LB multilayers of 4 as function of the layer thickness (cf. Example 27)

| Number of double layers transferred | $\sqrt[2]{I^{2\omega}}$ (relative units)* |
|---|---|
| 5 | 1.5 |
| 10 | 2 |
| 15 | 3.5 |
| 30 | 2.4 |
| 45 | 5.5 |
| 60 | 5.4 |
| 90 | 9.5 |
| 135 | 14 |
| 270 | 34 |

*The absolute efficiency of the frequency doubling is determined on 270 double layers (see text).

TABLE 10

Coupling angles and effective refractive indices for transmission in LB multilayers of 4 for different layer thicknesses (light vector parallel to the direction of dipping) (cf. Example 28)

| Number of double layers transferred | Coupling angle [degrees] | Effective refractive index $N_{eff}$ |
|---|---|---|
| 50 | 9.65 | 1.503 |
| 100 | 9.03 | 1.514 |
| 180 | 8.84 | 1.517 |

We claim:

1. A material in the form of a film comprising, in an oriented arrangement which does not display point symmetry, a compound of formula I

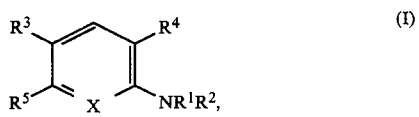

wherein X is =N—, $R^1$ is $C_{12}$–$C_{30}$-alkyl, $R^2$ is hydrogen or $C_1$–$C_{30}$-alkyl, $R^3$ is —$NO_2$, —CN, —$CF_3$, —$COOF_3$, —$SO_2CH_3$ or $SO_2CF_3$, $R^4$ is hydrogen or is defined in the same way as $R^3$, $R^5$ is hydrogen or —$NR^6R^7$ and $R^6$ and $R^7$ independently of one another are hydrogen or $C_1$–$C_{30}$-alkyl, wherein any of the alkyl radicals are optionally partially fluorinated or perfluorinated.

2. A material according to claim 1 wherein the compounds of formula I are arranged in the form of a Langmuir-Blodgett layer system.

3. A Languir-Blodgett layer system according to claim 2 containing alternating or non-alternating layers of compounds of formula I wherein X is =N—, $R^1$ is $C_{16}$–$C_{26}$-alkyl, $R^2$ is hydrogen, $R^3$ is —$NO_2$, $R^4$ is hydrogen or —$NO_2$ and $R^5$ is hydrogen.

4. A compound of formula I

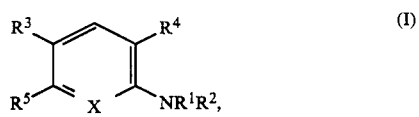

wherein X is =N—, $R^1$ is $C_{12}$–$C_{30}$-alkyl, $R^2$ is hydrogen or $C_1$–$C_{30}$-alkyl, $R^3$ is —$NO_2$, —CN, —$CF_3$, —$COCF_3$, —$SO_2CH_3$ or $SO_2CF_3$, $R^4$ is hydrogen or is defined in the same way as $R^3$, $R^5$ is hydrogen or —$NR^6R^7$ and $R^6$ and $R^7$ independently of one another are hydrogen or $C_1$–$C_{30}$-alkyl, wherein any of the alkyl radicals are optionally partially fluorinated or perfluorinated.

* * * * *